US012802820B2

(12) United States Patent
Liu et al.

(10) Patent No.: US 12,802,820 B2
(45) Date of Patent: Nov. 17, 2026

(54) COMPUTER IMPLEMENTED METHOD AND A SYSTEM

(71) Applicant: KONINKLIJKE PHILIPS N.V., Eindhoven (NL)

(72) Inventors: Jin Liu, Malden, MA (US); Lucas de Melo Oliveira, Wilmington, MA (US); Irina Waechter-Stehle, Hamburg (DE); Nils Thorben Gessert, Hamburg (DE); Simon Wehle, Hamburg (DE); David Prabhu, Cambridge, MA (US); Parastou Eslami, Cambridge, MA (US); Mathieu De Craene, Suresnes (FR); Antoine Olivier, Suresnes (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 18/719,494

(22) PCT Filed: Dec. 5, 2022

(86) PCT No.: PCT/EP2022/084339
§ 371 (c)(1),
(2) Date: Jun. 13, 2024

(87) PCT Pub. No.: WO2023/110477
PCT Pub. Date: Jun. 22, 2023

(65) Prior Publication Data

US 2025/0062022 A1 Feb. 20, 2025

(30) Foreign Application Priority Data

Dec. 16, 2021 (EP) .................................... 21290093

(51) Int. Cl.
*G16H 50/20* (2018.01)
*G16H 10/60* (2018.01)
(Continued)

(52) U.S. Cl.
CPC ............ *G16H 50/20* (2018.01); *G16H 10/60* (2018.01); *G16H 15/00* (2018.01); *G16H 30/20* (2018.01)

(58) Field of Classification Search
None
See application file for complete search history.

(56) References Cited

U.S. PATENT DOCUMENTS

2005/0119534 A1 6/2005 Trost et al.
2015/0066818 A1 3/2015 Choi et al.
(Continued)

FOREIGN PATENT DOCUMENTS

KR 20200063364 A 6/2020

OTHER PUBLICATIONS

Parmar et al. ("Data analysis strategies in medical imaging." Clinical cancer research 24.15 (2018): 3492-3499) (Year: 2018).*
(Continued)

*Primary Examiner* — Christopher B Tokarczyk

(57) ABSTRACT

A computer implemented method for collating patient data for analysis comprises receiving a set of input data comprising a plurality of patient data records, wherein the plural patient data records comprise medical imaging data and at least one other patient data type; and generating a vector for each of the plural patient data records by processing each patient data record using a corresponding encoding algorithm, wherein the encoding algorithm used to generate the vector is selected based on the type of patient data record and wherein the vectors are for use by a machine learning model.

13 Claims, 3 Drawing Sheets

(51) Int. Cl.
*G16H 15/00* (2018.01)
*G16H 30/20* (2018.01)

(56) References Cited

U.S. PATENT DOCUMENTS

| | | | | |
|---|---|---|---|---|
| 2016/0300034 | A1 | 10/2016 | Huddar et al. | |
| 2018/0144466 | A1 | 5/2018 | Hsieh et al. | |
| 2020/0146623 | A1 | 5/2020 | Anushiravani et al. | |
| 2020/0272857 | A1* | 8/2020 | Arcot Desai ....... | G06F 9/30036 |
| 2022/0147818 | A1* | 5/2022 | Zhang .................... | G06N 3/045 |

OTHER PUBLICATIONS

International Search Report and Written Opinion for PCT/EP2022/084339; Mailing date: Mar. 13, 2023, 10 pages.

* cited by examiner

COMPUTER IMPLEMENTED METHOD AND A SYSTEM

CROSS-REFERENCE TO PRIOR APPLICATIONS

This application is the U.S. National Phase application under 35 U.S.C. § 371 of International Application No. PCT/EP2022/084339, filed on Dec. 5, 2022, which claims the benefit of European Patent Application No. 21290093.0, filed on Dec. 16, 2021. These applications are hereby incorporated by reference herein.

FIELD OF THE INVENTION

A computer implemented method for collating patient data for analysis and a system for collating patient data for analysis.

BACKGROUND OF THE INVENTION

Assessment of a patients' health, and in particular prediction of future health, such as disease onset prediction and disease progression prediction, is essential for treatment plan decisions. There is rich longitudinal information (i.e. information obtained over time) in the form of patient's healthcare records, both directly related to a particular condition and in general. In terms of general data, assessment of health or a particular condition is often affected by the particular patient (e.g. age, gender) and lifestyle (e.g. diet, smoking status), all of which can affect disease likelihood or progression. Where a patient is already being monitored or undergoing investigation for a condition, there will usually be plural studies over time with different information and, in many cases, investigation reports such as imaging data or physiological data. All of this can be used to identify risks or health issues, and predict onset or progression.

However, the data are usually very complex and heterogeneous, and it is difficult to assimilate this information in such a way that it can all be taken into account. For example, manually reviewing this can be laborious and is subject to a particular medical professional's experience and expertise and can be error prone or inaccurate. Automated analysis is limited by the heterogeneous nature of the data.

US2018144466A1 discloses methods and apparatus for improved deep learning for image acquisition. The example apparatus includes a deployed learning device including a second processor to implement a second DLN, the second DLN generated from the first DLN of the training learning device, the deployed learning device configured to provide a second imaging system configuration parameter to the imaging system in response to receiving a second input for image acquisition.

SUMMARY OF THE INVENTION

In a first aspect of the invention, there is provided a computer implemented method for collating patient data for analysis, the method comprising: receiving a set of input data comprising a plurality of patient data records, wherein the plural patient data records comprise medical imaging data and at least one other patient data type: and generating a vector for each of the plural patient data records by processing each patient data record using a corresponding encoding algorithm, wherein the encoding algorithm used to generate the vector is selected based on the type of patient data record and wherein the vectors are for use by a machine learning model.

Embodiments provide a method of pre-processing heterogeneous data types, specifically different types of patient data (patient data records) which enables the subsequent processing of these to provide an output relating to the heath of a patient or a particular condition. This can improve the accuracy and the sensitivity of an output, as subsequent analysis is not limited to a particular data-type and does not apply an unintended weighting to a particular data-type. The data may be obtainable from a medical record (e.g. an electronic medical record (EMR), radiologic information systems, cardiology information systems and/or picture archiving and communication system (PACS)), and therefore can combine significant amounts of heterogeneous patient data.

In particular, the use of the vectorization process better preserves important information held in each of the different data types, since the nature and location of the most important information for various medical inputs will be different. For example, compared to a system which assimilates the data using a single encoding algorithm, embodiments provide a method in which the heterogeneous data from each record is encoded (i.e. a feature vector is generated) using an algorithm or model that is appropriate or optimized for that particular data type. This ensures that the data integrity is maintained and the key aspects of each record are retained for subsequent processing and can improve both accuracy and sensitivity of subsequent analysis. Moreover, this overcomes issues associated with different data models, formats, and semantics associated with the data-types. The vectors can then be combined/analyzed to determine the output.

Each encoding algorithm may be a model specific to a data-type (e.g. specific to medical imaging data or a specific type of medical imaging data, or non-medical imaging data or a specific type of non-imaging medical data). The model can be used to convert the data into the vector(s). The encoding algorithm may be a deep learning algorithm, traditional machine learning, signal processing, and/or statistical models. Examples of deep learning models include but are not limited to convolutional neural networks (e.g. 3D convolutional networks), transformer neural networks, and fully connected networks. In some embodiments, the models are machine learning models, such as a neural network (e.g. 3D convolutional network, fully connected network).

This pre-processing enables the use of a machine learning model or algorithm to provide an output relating to the health of the patient (e.g. a prediction relating to the onset or progression of a condition), such an output being more accurate and more sensitive to changes due to the data-type-specific pre-processing steps.

At least one of the data inputs (i.e. patient data records or "patient data") comprises medical imaging data, and correspondingly the generation of a vector based on the medical imaging data record comprises using an encoding algorithm that is specific to medical imaging data, and in some cases specific to the particular type of medical imaging data. Medical imaging data can include scans or frames of a particular anatomical region, including for example 2D, 3D, 2D+t or 3D+t medical imaging data (e.g. ultrasound imaging, MRI imaging).

The at least one other type of data is a different type of data to the medical imaging data-type (this may be a different model, in a different format or having different semantics), such that a different encoding algorithm is used to pre-process the data. In some embodiments, this may be a different medical imaging data-type (e.g. obtained by a different modality) and/or a non-medical imaging data type (e.g. as physiological data (e.g. a signal, such as an ECG signal) or text-based medical data (e.g., a medical exam/diagnosis report)). In an embodiment, at least one other patient data type is non-medical imaging data relating to a patient. In an embodiment of the computer implemented method, the non-image medical data comprises physiological data. In an embodiment of the computer implemented method, non-medical imaging data is in the form of at least one of text-based data, signal data, and tabular data.

The data received and analyzed may relate to a single patient so that the output relates to a single patient. The data used in the method can be obtained from a single point in time (e.g. a single study or investigation) or may have been obtained from a plurality of points in time (e.g. different studies or investigations, occurring at different times (e.g. days)). The data used may pertain to a particular condition (e.g. studies directed to monitoring or assessing a condition), or may comprise taking into account more general health which may contribute to a particular condition.

In an embodiment, the computer implemented method further comprises analyzing the vectors using a machine learning model; and producing an output containing information relating to a patient's health. In such embodiments, the method is accordingly for providing or producing an output containing information relating to a patient's health.

The use of machine learning, through a machine learning engine or model (this can be e.g. a classification/regression model using traditional machine learning models or deep learning models), provides additional benefits as the output can be more accurate and sensitive as more subtle changes over time can be detected. In embodiments, the machine learning model receives the inputs in the form of the features vectors and uses a machine learning engine to determine the output e.g. changes between the data (e.g. images) over time. The machine learning model may be trained such that the machine learning model is able to provide the output. In some embodiments, a training database may be provided which may contain training information including images and the associated outputs.

In an embodiment, the method further comprises combining the vectors prior to analyzing the vectors. Combining the output vectors can be carried out using a number of different ways, such as stacking the vectors as a one-dimensional vector or multidimensional vectors. Accordingly, in an embodiment of the computer implemented method, combining the vectors comprises combining the vectors to form a one-dimensional or multidimensional vector. The computer implemented method's ability, in some embodiments, to process multiple types of data including both image, signal and non-image data through time allows for significant improvements in accuracy to be made over previous attempts to predict disease onset or progression.

In an embodiment, the output of the computer implemented method comprises a prediction pertaining to the diagnosis, onset and/or progression of a disease for a patient. Producing an output containing information regarding the diagnosis, onset and/or progression of disease is of benefit since it can be used by a medical practitioner to obtain information that would not have otherwise been easily obtainable. Having a predictive model that takes into account a vector that contains a plurality of patient data records rather than a single record allows for more accurate predictions to be made regarding the diagnosis, onset and/or progression of disease. In such embodiments, the method is accordingly for providing or producing a prediction pertaining to the diagnosis, onset and/or progression of a disease for a patient.

In an embodiment of the computer implemented method, the machine learning model is a recursive and/or recurrent model, such as a recursive neural network. Embodiments where the data used in the method has been obtained at different time points (i.e. longitudinal data) and recurrent/recursive models (such as a recursive neural network) are used can be particularly advantages as the temporal aspect can be taken into account. For example, the time the data was obtained can be used to weight the analysis. Examples include gated recurrent units (GRUs), long short-term memory (LSTM) cells, or other recurrent models.

In an embodiment., the plurality of patient data records comprise patient data records obtained at a plurality of points in time; and wherein analyzing the vectors using a machine learning model comprising applying a weighting to each patient data record based on the point in time that the record was created. The weighting may apply more weight to the more recently obtained data, in some embodiments. An example of this may be weighting a scan that has been taken recently more heavily than a scan that was taken at an earlier point in time. This enables the accuracy of predictions pertaining to the diagnosis, onset and/or progression of a disease to be improved. Although some risk scores have developed (e.g. Framingham risk score) for disease prediction, these are general and only depend on one study or investigation. Embodiments taking into account longitudinal data for disease prediction provide improved accuracy over these by taking into account data obtained over time and monitoring the changes.

This is also particularly advantageous as there is almost always a vast amount of longitudinal information in a patient's medical records, and the healthcare system more generally, which can be used in such an analysis.

In one embodiment where the patient data comprises data obtained at plural points in time (e.g. different days or studies), each patient data comprises time stamps associated therewith and generation of the vector comprises time-resolved feature vectors based on the time stamps. In such embodiments, subsequent processing determines the disease onset/progress prediction based on a plurality of time-resolved feature vectors. In these embodiments, the vector(s) can be analyzed with a recurrent model (such as a recurrent/recursive neural network (RNN) and/or long short-term memory (LSTM)). These can be used to analyze the temporal information to provide more accurate and improved outputs.

In an embodiment, the machine learning model is trained. Training can occur prior to or as part of the analysis of the vectors using the machine learning model. In one embodiment, training is carried out using medical data duplets, each medical data duplet comprising: (i) a plurality of patient data records of a respective patient; and (ii) disease diagnosis and/or progression data for the patient.

The computer implemented method is able to process several types of data, including medical imaging data. There is therefore a large pool of potential training data which has been taken over time which may be used to train this machine learning model.

In an embodiment, generating a vector for each of the plural patient data records by processing each patient data record using a corresponding encoding algorithm is carried out using a neural network model, traditional machine learning model, signal processing and/or statistical model. These, such as a neural network, may be trained with data such that the performance improves over time. Improvements in encoding algorithms have the potential to decrease the processing power and time required to produce a vector. In an embodiment, the neural network is a convolutional neural network, transformer neural network, or a fully connected neural network. Convolutional neural networks are particularly effective for processing medical imaging data, ensuring that the important information is retained in the vector.

In an embodiment, the medical imaging data is in the form of two or three dimensional data.

In an embodiment, the plurality of patient data records comprise patient data records obtained at a plurality of points in time; and generating a vector for each of the plural patient data record comprises generating time-resolved feature vectors.

In an embodiment, the patient data records comprise patient demographic data. This can be scalar data such that a vector of scalar data is produced.

In one embodiment, the plurality of patient data records comprises: (i) a first patient data record comprising at least one medical image (i.e. medical imaging data); (ii) a second patient data record comprising a non-image medical data comprising a physiological signal; and (iii) a third patient data record comprising text-based medical data. This combination of data is traditionally particularly difficult to combine but the disclosed methods provide improved preprocessing that enables the more accurate determination of health parameters using these three data types.

In a second aspect of the invention, there is provided a system for collating patient data for analysis, the system comprising: a memory comprising instruction data representing a set of instructions; and one or more processors configured to communicate with the memory and to execute the set of instructions, wherein the set of instructions, when executed by the processor cause the processor to carry out the aforementioned computer implemented method.

It should be understood that when referring to the processing that takes place in the method it is not limited the method to being carried out by a single processor or computer. Instead, the method may be carried out by plural processors which may be provided at different locations and interconnected, for example, using a distributed network. An example of this may be the processing of images from multiple data sources that have been transferred or stored on a distributed network (e.g. a "cloud"-based network). Furthermore, any processing stages may occur on different processors within a network.

A processor may be implemented in any suitable manner, with software and/or hardware, to perform the various functions required. Examples of processor components that may be employed in various embodiments of the present disclosure include, but are not limited to, conventional microprocessors, application specific integrated circuits (ASICs), and field-programmable gate arrays (FPGAs). The processor may be associated with one or more non-transitory storage media such as volatile and non-volatile computer memory such as RAM, PROM, EPROM, and EEPROM. The non-transitory storage media may be encoded with one or more programs that, when executed on one or more processors and/or controllers, perform the required functions. Various storage media may be fixed within a processor or controller or may be transportable, such that the one or more programs stored thereon can be loaded into the signal processing unit, property determination unit and/or processor.

In embodiments, the system includes a user interface, such as a display, for displaying the output. Alternatively or additionally, the system may include a communications interface device, such as a wireless transmitter, configured to transmit the output to an external device, such as a personal computer, tablet, smartphone, remote server, etc.

In a third aspect, there is provided a method for collating patient data for analysis (such as a method for predicting the diagnosis, progression or onset of a disease) the method comprising (i) obtaining of input data comprising a plurality of patient data records, wherein the plural patient data records comprise medical imaging data and at least one other patient data type; and (ii) generating a vector for each of the plural patient data records by processing each patient data record using a corresponding encoding algorithm, wherein the encoding algorithm used to generate the vector is selected based on the type of patient data record and wherein the vectors are for use by a machine learning model. The method may use the computer implemented method as set out in respect of any of the embodiments defined herein.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
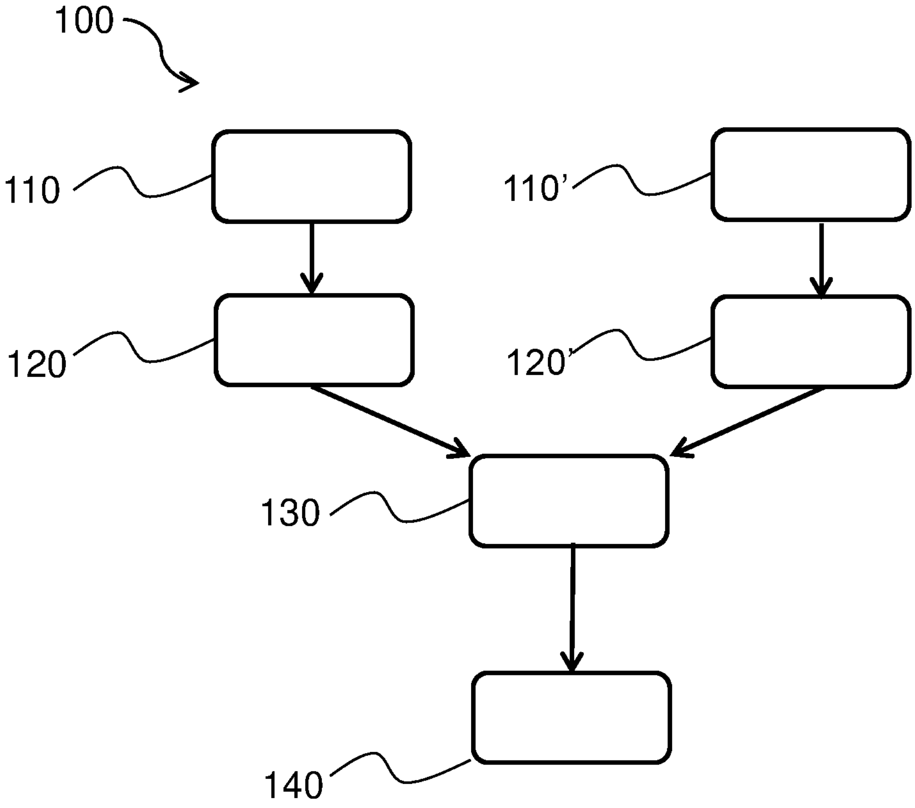
FIG. 1 provides a schematic diagram of a computer implemented method according to an embodiment of the invention.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfil the functions of several items recited in the claims. The mere fact that certain measures are recited in mutually different dependent claims does not indicate that a combination of these measures cannot be used to advantage.

If the term "adapted to" is used in the claims or description, it is noted the term "adapted to" is intended to be equivalent to the term "configured to".

Any reference signs in the claims should not be construed as limiting the scope.

FIG. 1 provides a schematic overview of a computer implemented method for collating patient data for analysis 100, which method 100 is used to provide an output containing information relating to a patient's health 140.

The method 100 as depicted includes two separate branches corresponding to two different patient data types (relating to a single patient). Specifically, the method 100 comprises receiving a set of input data comprising receiving medical imaging data 110 and receiving non-medical imaging patient data 110'. In embodiments, the medical imaging data may be in the form of 2D, 3D, 2D+t, or 3D+t data (such as ultrasound or MRI imaging data). The non-medical can be, in some embodiments, text-based data (e.g. text-based medical test data, examination results, diagnosis and patient demographic information) or physiological signals.

Accordingly, the data received is heterogeneous. In this embodiment, the medical imaging data and non-medical imaging data are related in that they have relevance to a health condition under investigation. The input data may be extracted or received from a healthcare database or plural databases. For example, this data may be extracted or received from EMRs, Radiology Information System, Cardiology Information System and/or PACS. Alternatively, this may be extracted or received from the devices or instruments used to obtain the data, such as a medical device or sensor. Interfacing with clinical, operational, and demographic data sources can be done with any available state-of-art IT communication protocol such as HL7, DICOM and FHIR.

Each data-type is prepared (pre-processed) separately. The method 100 therefore further comprises generating a first vector 120 for the medical imaging data received in the first step 110. Generating the first vector 120 comprises processing each patient data record (i.e. the medical imaging data in this case) using an encoding algorithm which is optimized and specific to medical imaging data. The encoding algorithm may be an AI or machine learning algorithm or model. Examples for medical imaging data include but are not limited to convolutional neural networks (e.g. 3D convolutional networks) and fully connected network.

The method 100 also comprises generating a second vector 120' for the non-medical imaging data received in the first step 110'. In this case, generating the vector 120' comprises processing each patient data record (i.e. the non-medical imaging data in this case) using an encoding algorithm which is optimized and specific to the specific data type. This is a different encoding algorithm to that used to encode the first vector such that the data extraction is optimized for each data type thereby providing an output that is especially accurate and that key aspects and information in each particular data type is retained and taken into account in subsequent processing.

Accordingly, for each type of patient data, a model that is suitable for the data type can be built. These model wills convert the data into vectors from different data sources.

The method 100 further comprises analyzing the vectors using a machine learning model 130. This includes analysis and combination of the vectors so as to provide an output containing information relating to a patient's health 140 which takes into account the plural different inputs received in the first steps 110, 110".

The output can be in a number of forms. It may comprise an indication of health (such as diagnosis) or may comprise a prediction regarding the diagnosis, onset and/or progression of a disease (e.g. expected progression). It may comprise a medical image or model indicating regions of particular interest or similar. The output may be provided on a display of an associated system.

The general method 100 of FIG. 1 can be used to process different data types obtained at a single point in time (i.e. as part of a single investigation or study of the patient) or may be used to process different data types obtained at different points in time (e.g. obtained as part of different investigations or studies of the patient or taking across a period of time). In other embodiments, the data may be obtained at different points in time but the time it was obtained or recorded may not be taken into account. In such an embodiment, it is treated like data obtained at a single point in time.

Where the data is obtained at a single point in time (or where the time information is not taken into account), the output vectors from the step of generating the vectors 120, 120' can be supplied to a regression/classification model for training. This may also further comprise using historical disease diagnosis and/or progression information, the classification/regression model could be trained using traditional machine learning models or deep learning models.

Where the data is obtained at plural points in time and the time factor (i.e. temporal aspect) is to be taken into account, the output vectors from the step of generating the vectors 120, 120' can be supplied to a recursive/recurrent model (e.g. recurrent neural network, RNN and/or long short-term memory (LSTM)) for disease training. The step of combining may first comprise combining the plural time vectors as stacked one-dimensional vector or multidimensional vectors. The use of a recurrent model such as RNN and/or long short-term memory (LSTM) can be used to analyze the temporal information to provide more accurate and improved outputs. The vectors generated in the step 130 may be time-resolved feature vectors.

Figure 2:
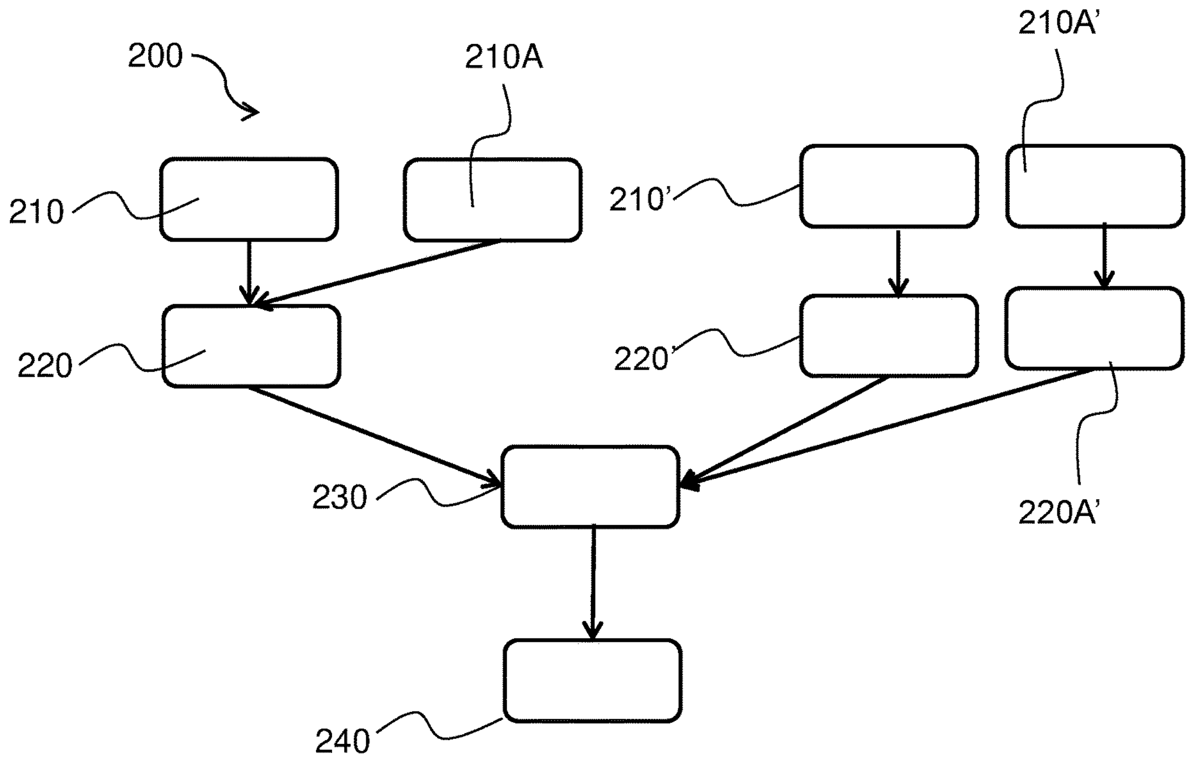
FIG. 2 provides a schematic diagram of a computer implemented method according to another embodiment of the invention.

FIG. 2 shows a second embodiment of a method of providing a prediction relating to the onset of a disease or condition 200. In this embodiment, there are plural data types and within each data type, plural patient records obtained at different times. This is depicted as two main branches corresponding to two different data types, and two sub-branches each corresponding to the different points in time that the data was obtained.

As shown in the first branch, the method 200 comprises receiving a set of input data comprising receiving medical imaging data obtained at a first point in time 210 and receiving the same type of medical imaging data but obtained at a second different point in time 210A. This may be, for example, a first image corresponding to a scan of an anatomical region obtained at a first date and a second image corresponding to the same type of scan of the same region obtained at a later date, as is common in monitoring disease progression.

The input data also includes non-medical imaging patient data such that the method also comprises receiving non-medical imaging patient data obtained at a first point in time 210' (this need not correspond to the same point in time as the medical imaging data was obtained) and receiving non-medical imaging patient data obtained at a second point in time 210A' (this need not correspond to the same point in time as the medical imaging data was obtained).

The method 200 further comprises generating vectors 220, 220', 200A" based on this input data. Specifically each type of data is prepared (processed) separately.

In this embodiment, the method 200 further comprises generating vectors for the medical imaging data 220 received in the first step 210, 210A. This comprises processing each patient data record (i.e. the plural medical imaging data in this case) using an encoding algorithm which is optimized and specific to medical imaging data. In this embodiment, the date the medical imaging data was obtained is encoded into the resultant vectors to produce time-resolved vectors. Purely as an example, in one embodiment, these can be combined into a single time-resolved vector prior to analysis as part of step 220. In other embodiments, these can be provided as separate vectors to the analysis model in the subsequent step.

The method also comprises generating second vectors 220', 220A' for the non-medical imaging data received in the first step 210', 210A'. This comprises processing each patient data record (i.e. the plural non-imaging data in this case) using an encoding algorithm which is optimized and specific to the specific type of non-imaging data. In this embodiment, the date the data was obtained is encoded into the resultant vectors to produce corresponding time-resolved vectors. Purely as an example, in this embodiment, these are provided as separate vectors to the analysis model in the subsequent step. In other embodiments, these can be combined into a single time-resolved vector prior to analysis.

The method 200 further comprises analyzing the vectors using a machine learning model 230. This includes analysis and combination of the vectors so as to provide an output containing information relating to a patient's health 240 which takes into account the plural different inputs received in the first steps 210, 210A, 210', 210A' and the temporal aspect of the data.

The machine learning model used in the analysis step of the abovementioned embodiments can be trained using duplets of information. Each medical data duplet can comprise a plurality of datasets of medical data of different types of a respective patient; and disease diagnosis and/or progression data for said respective patient. In this way, the model can be trained to determine the indicators of a particular disease and improve the accuracy of the prediction. Where temporal data is used, this can also be used to refine predictions relating to the onset or progression of the condition in question.

Figure 3:
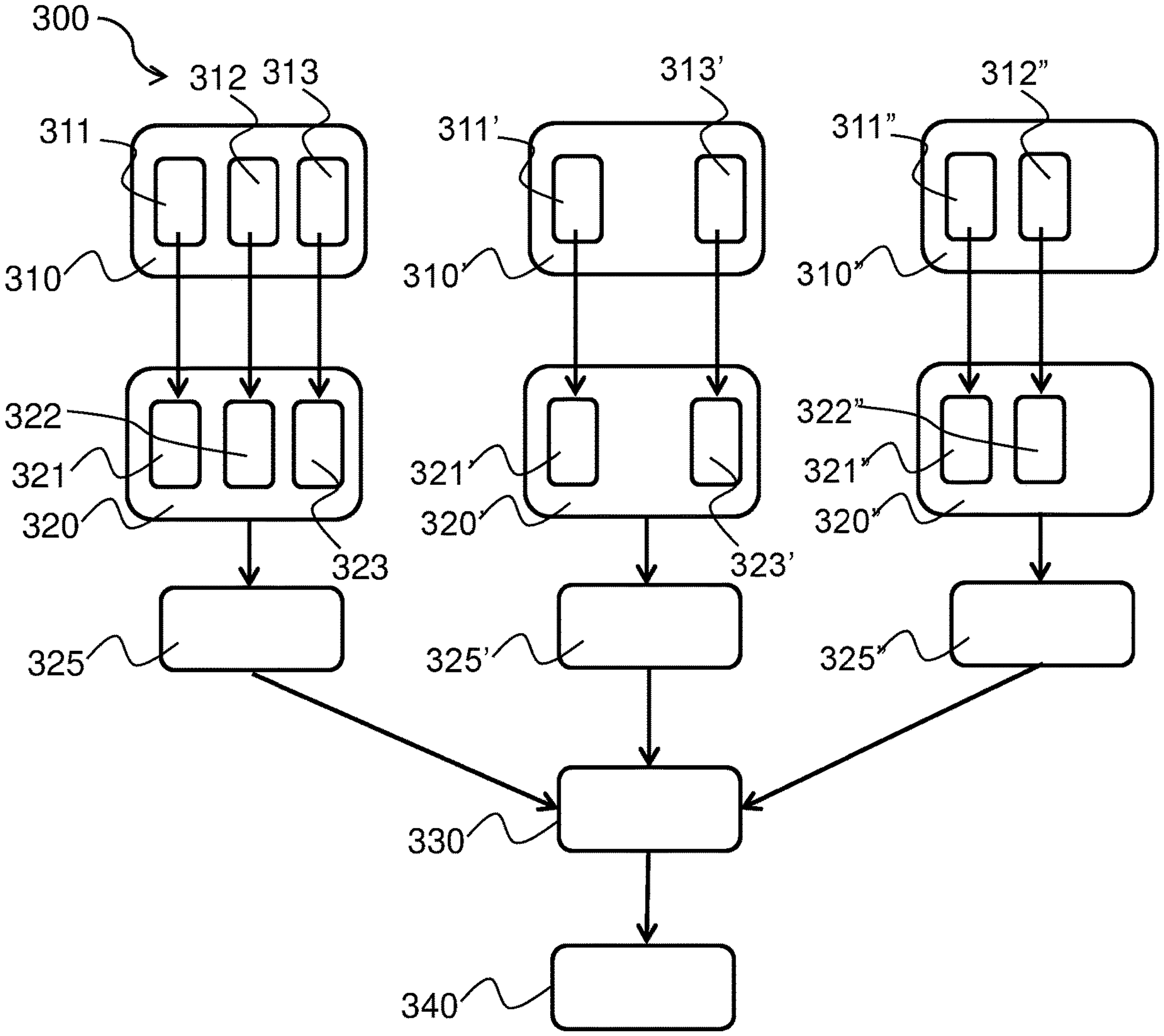
FIG. 3 provides a schematic diagram of a computer implemented method according to another embodiment of the invention.

FIG. 3 schematically depicts a further embodiment of a method of providing a prediction relating to the onset of a condition for a patient 300.

The method in this embodiment receives a set of input data 310, 310', 310" comprising three distinct sets of data corresponding to three different points in time. Thus, the method comprises receiving first medical data 310 relating a relating to a patient obtained at a first time point, receiving second medical data 310' relating a relating to a patient obtained at a second time point, and receiving third medical data 310" relating a relating to a patient obtained at a this time point.

In this embodiment, the first medical data includes medical image data 311, medical data relating to a physiological signal 312 and text-based medical data relating to a diagnosis report 313, all obtained at a first time point as part of a first study. The second medical data includes medical image data 311' and text-based medical data relating to a diagnosis report 313', all obtained at a second time point as part of a second study. The third medical data includes medical image data 311" and medical data relating to a physiological signal 312", all obtained at a third time point as part of a third study.

The method 300 in this embodiment individually processes each data type within each study (per-study) using a predetermined and data-type-specific encoding algorithm, thereby generating individual vectors for each data type within each study. The plural vectors for each study are then combined (within each study) to provide a multi-dimensional or stacked vector for each study. These are each encoded with time specific information so that temporal analysis can occur.

Specifically, the method 300 further comprises generating vectors for the first data set 320, which itself comprises generating a first vector for the medical imaging data 321 using a medical imaging encoding model (i.e. a model adapted or configured for converting medical imaging data into a vector), generating a second vector for the medical data relating to a physiological signal 322 using a physiological signal encoding model (i.e. a model adapted or configured for converting physiological signal data into a vector) and generating a third vector for the text-based medical data 323 using a text-based data encoding model (i.e. a model adapted or configured for converting text-based data into a vector). These are subsequently combined 325 to provide a multi-dimensional or stacked vector encoding temporal information. The use of data-type-specific models ensures that all of the key information present in each of the data is retained and encoded into the vectors.

The method 300 also comprises generating vectors for the second set 320', which comprises generating a first vector for the medical imaging data 321' using a medical imaging encoding model and generating a second vector for the text-based medical data 323' using a text-based data encoding model. These are subsequently combined 325' to provide a multi-dimensional or stacked vector encoding temporal information.

The method 300 further comprises generating vectors for the third data set 320", which comprises generating a first vector for the medical imaging data 321" using a medical imaging encoding model and generating a second vector for the medical data relating to a physiological signal 322" using a physiological signal encoding model. These are subsequently combined 325" to provide a multi-dimensional or stacked vector encoding temporal information.

The resultant vectors from this process are then combined and analyzed in a subsequent processing step 330. In particular, the vectors are used to train a machine learning model, which in this embodiment comprises a recurrent neural network which analyses and takes into account the temporal aspect of the data. The method in this embodiment includes applying a weighting to each patient data record based on the point in time that the record was created.

The result from the analysis is an output 340 in the form of a prediction relating to the onset of a condition for a patient, which takes account of the three studies and the data within each of the studies.

Although the invention has been described with reference to specific embodiments and examples above, it will be appreciated that modifications can be made to the embodiments and examples without departing from the invention.

The invention claimed is:

1. A computer implemented method for collating patient data for analysis, the method comprising:

receiving a set of input data comprising a plurality of patient data records, wherein the plurality of patient data records comprise medical imaging data and at least one other patient data type;

selecting an encoding algorithm from a plurality of encoding algorithms for each of the plurality of patient data records, wherein the encoding algorithm is selected based on a patient data type of a plurality of patient data types, wherein the medical imaging data and the at least one other patient data type are included in the plurality of patient data types;

generating a first vector for each of the plurality of patient data records by processing each patient data record at a first time using the encoding algorithm selected for each of the plurality of patient data records at the first time;

generating a second vector for each of the plurality of patient data records by processing each patient data record at a second time using the encoding algorithm selected for each of the plurality of patient data records at the second time;

combining the first vector and the second vector to generate a single time-resolved vector;

analyzing the single time-resolved vector with a machine learning model; and providing from the machine learning model an output containing information relating to a patient's health.

2. The method according to claim 1, wherein the output is a prediction pertaining to a diagnosis, an onset and/or a progression of a disease for the patient.

3. The method according to claim 1, wherein the machine learning model is a recursive model and/or recurrent model.

4. The method according to claim 1, wherein generating the first vector and the second vector comprises applying a weighting to the first vector and the second vector based on the first time and the second time.

5. The method according to claim 1, wherein the machine learning model is trained using medical data duplets, each medical data duplet comprising:

a plurality of patient data records of a respective patient; and disease diagnosis and/or progression data for the patient.

6. The method according to claim 1, wherein the at least one other patient data type is non-medical imaging data relating to a patient.

7. The method according to claim 6, wherein the non-image medical data comprises physiological data.

8. The method according to claim 6, wherein non-medical imaging data is in the form of at least one of text-based data, signal data, and tabular data.

9. The method according to claim 1, wherein generating the first vector and the second vector for each of the plurality of patient data records by processing each patient data record using the encoding algorithm selected is carried out using a neural network model, a traditional machine learning model, signal processing and/or a statistical model.

10. The method according to claim 9, wherein the neural network is a convolutional neural network, a transformer neural network, or a fully connected neural network.

11. A system for collating patient data for analysis, the system comprising:

a memory comprising instruction data representing a set of instructions; and one or more processors configured to communicate with the memory and to execute the set of instructions, wherein the set of instructions, when executed by the processor cause the processor to carry out the computer implemented method given in claim 1.

12. The method of claim 1, wherein the first vector and second vector retain aspects of the patient data type of the patient data record.

13. The method of claim 1, wherein the machine learning model is trained based on temporal features included in the plurality of patient data records.

* * * * *